United States Patent
Leung et al.

(10) Patent No.: US 9,750,550 B2
(45) Date of Patent: Sep. 5, 2017

(54) CONTOURED BONE PLATE

(71) Applicant: Biomet Manufacturing, LLC, Warsaw, IN (US)

(72) Inventors: Ross T. Leung, Piscataway, NJ (US); Jordan N. Milford, Bethlehem, PA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 280 days.

(21) Appl. No.: 14/564,185

(22) Filed: Dec. 9, 2014

(65) Prior Publication Data

US 2015/0094810 A1   Apr. 2, 2015

Related U.S. Application Data

(63) Continuation of application No. 11/627,018, filed on Jan. 25, 2007, now Pat. No. 8,926,675.

(60) Provisional application No. 60/791,228, filed on Apr. 11, 2006.

(51) Int. Cl.
| | |
|---|---|
| *A61B 17/80* | (2006.01) |
| *A61F 2/46* | (2006.01) |
| *A61B 17/34* | (2006.01) |
| *A61B 17/84* | (2006.01) |

(52) U.S. Cl.
CPC .......... *A61B 17/80* (2013.01); *A61B 17/3472* (2013.01); *A61F 2/4601* (2013.01); *A61B 17/8057* (2013.01); *A61B 17/842* (2013.01)

(58) Field of Classification Search
USPC .............................. 606/70, 71, 74, 280–299
See application file for complete search history.

(56) References Cited

U.S. PATENT DOCUMENTS

| | | | |
|---|---|---|---|
| 3,463,148 | A | 8/1969 | Treace |
| 3,716,050 | A | 2/1973 | Johnston |
| 5,709,686 | A | 1/1998 | Talos et al. |
| 5,938,664 | A | 8/1999 | Winquist et al. |
| 6,001,099 | A | 12/1999 | Huebner |
| 6,093,201 | A * | 7/2000 | Cooper .................. A61B 17/80 606/232 |
| 6,096,040 | A | 8/2000 | Esser |
| D443,060 | S | 5/2001 | Benirschke et al. |
| 6,228,085 | B1 | 5/2001 | Theken et al. |

(Continued)

OTHER PUBLICATIONS

Non-Final Office Action regarding U.S. Appl. No. 11/627,018, mailed Apr. 2, 2014.

(Continued)

*Primary Examiner* — Matthew Lawson
(74) *Attorney, Agent, or Firm* — Schwegman Lundberg & Woessner, P.A.

(57) ABSTRACT

A method for repairing a bone includes attaching a bone plate to the bone. The bone plate includes an upper surface, a bone-contacting surface, and at least one hole extending between the upper surface and the bone-contacting surface. The method also includes inserting at least a portion of a delivery device into the at least one hole. The delivery device includes at least one of an osteobiologic material, a graft material and a pharmacological substance. The method further includes injecting the at least one of the osteobiologic material, the graft material and the pharmacological substance into the bone and through the at least one hole.

20 Claims, 6 Drawing Sheets

(56) References Cited

U.S. PATENT DOCUMENTS

| | | |
|---|---|---|
| 6,238,969 B1 | 5/2001 | Figura et al. |
| 6,309,393 B1 | 10/2001 | Tepic et al. |
| 6,355,042 B2 | 3/2002 | Winquist et al. |
| D458,684 S | 6/2002 | Bryant et al. |
| D458,996 S | 6/2002 | Bryant et al. |
| D463,557 S | 9/2002 | Bryant et al. |
| D463,558 S | 9/2002 | Bryant et al. |
| D463,559 S | 9/2002 | Bryant et al. |
| D464,136 S | 10/2002 | Bryant et al. |
| D464,731 S | 10/2002 | Bryant et al. |
| D470,588 S | 2/2003 | Bryant et al. |
| 6,623,486 B1 | 9/2003 | Weaver et al. |
| 6,669,701 B2 | 12/2003 | Steiner et al. |
| 6,709,686 B1 | 3/2004 | Matthew |
| 6,719,759 B2 | 4/2004 | Wagner et al. |
| 6,730,091 B1 | 5/2004 | Pfefferle et al. |
| 6,955,677 B2 | 10/2005 | Dahners |
| 7,001,388 B2 | 2/2006 | Orbay et al. |
| 8,926,675 B2 | 1/2015 | Leung et al. |
| 2004/0059334 A1 | 3/2004 | Weaver et al. |
| 2004/0059335 A1 | 3/2004 | Weaver et al. |
| 2004/0102777 A1 | 5/2004 | Huebner |
| 2004/0116930 A1 | 6/2004 | O'Driscoll et al. |
| 2004/0193162 A1* | 9/2004 | Bramlet ............... A61B 17/746 606/66 |
| 2005/0010226 A1 | 1/2005 | Grady et al. |
| 2005/0015089 A1 | 1/2005 | Young et al. |
| 2005/0070904 A1 | 3/2005 | Gerlach et al. |
| 2005/0080421 A1 | 4/2005 | Weaver et al. |
| 2005/0107796 A1 | 5/2005 | Gerlach et al. |
| 2005/0182405 A1 | 8/2005 | Orbay et al. |
| 2005/0182406 A1 | 8/2005 | Orbay et al. |
| 2005/0240187 A1 | 10/2005 | Huebner et al. |
| 2006/0004361 A1 | 1/2006 | Hayeck et al. |
| 2006/0004362 A1 | 1/2006 | Patterson et al. |
| 2006/0009771 A1 | 1/2006 | Orbay et al. |
| 2006/0035772 A1 | 2/2006 | Golesh et al. |
| 2006/0116679 A1 | 6/2006 | Lutz et al. |
| 2006/0173458 A1 | 8/2006 | Forstein et al. |
| 2006/0235400 A1 | 10/2006 | Schneider |
| 2006/0241617 A1* | 10/2006 | Holloway ............... A61B 17/80 606/70 |
| 2006/0264947 A1* | 11/2006 | Orbay ............... A61B 17/1615 606/291 |
| 2006/0276896 A1 | 12/2006 | Fallin et al. |
| 2007/0083207 A1 | 4/2007 | Ziolo et al. |
| 2007/0088360 A1 | 4/2007 | Orbay et al. |
| 2007/0093835 A1 | 4/2007 | Orbay et al. |
| 2007/0173843 A1* | 7/2007 | Matityahu ............... A61B 17/80 606/916 |

OTHER PUBLICATIONS

Non-Final Office Action regarding U.S. Appl. No. 11/627,018, mailed Dec. 12, 2013.

Final Office Action regarding U.S. Appl. No. 11/627,018, mailed Oct. 26, 2009.

Non-Final Office Action regarding U.S. Appl. No. 11/627,018, mailed Mar. 5, 2009.

* cited by examiner

CONTOURED BONE PLATE

CROSS-REFERENCE TO RELATED APPLICATIONS

This application is a continuation of U.S. patent application Ser. No. 11/627,018, filed on Jan. 25, 2007, which claims the benefit of U.S. Provisional Application No. 60/791,228, filed on Apr. 11, 2006. The disclosure of the above application is incorporated herein by reference.

INTRODUCTION

There are numerous orthopaedic bone plates for the femur and tibia that have surfaces approximating the corresponding human bone surfaces. One reason for such design is to diminish possible soft tissue irritation by the implanted plate. However, when such plates are implanted with bone anchors, such as screws or other fasteners, irritation of the surrounding soft tissues may still occur, because an otherwise smooth surface becomes interrupted by the heads of the bone anchors, portions of which may protrude in various directions.

Thus there is still a need for procedures and plating assemblies that may further reduce soft tissue irritation.

SUMMARY

The present teachings provide a method for repairing a bone. The method can include attaching a bone plate to the bone. The bone plate may include an upper surface, a bone-contacting surface, and at least one hole extending between the upper surface and the bone-contacting surface. The method can also include inserting at least a portion of a delivery device into the at least one hole. The delivery device can include at least one of an osteobiologic material, a graft material and a pharmacological substance. The method can further include injecting the at least one of the osteobiologic material, the graft material and the pharmacological substance into the bone and through the at least one hole.

In another aspect, the present teachings provide a method for implanting a bone plate. The method can include attaching the bone plate to a bone. The bone plate can include an upper surface, a bone-contacting surface, a fastener hole, a suture hole, and a graft hole. The fastener, suture and graft holes can extend between the upper surface and the bone-contacting surface. The method can also include inserting a fastener through the fastener hole and into the bone, and inserting a suture through the suture hole. The method can further include providing a syringe having a tip portion, an outer tube, and a plunger, and loading the outer tube with at least one of an osteobiologic material, a graft material and a pharmacological substance. The method can also include inserting the tip portion of the syringe into the graft hole and injecting the at least one of the osteobiologic material, the graft material and the pharmacological substance through the tip portion and into the graft hole.

In yet another aspect, the present teachings provide an orthopaedic assembly. The orthopaedic assembly can include a bone plate and a delivery device. The bone plate can be attachable to a bone and can include an upper surface, a bone-contacting surface, and an undulating perimeter. The upper surface and the bone-contacting surface can cooperate to define a nominal thickness of the bone plate. The undulating perimeter can extend from and between the upper surface and the bone-contacting surface and can define a plurality of suture-clearance formations. The plurality of suture-clearance formation can provide a clearance between the bone-contacting surface of the bone plate and the bone. A plurality of suture holes can extend between the upper surface and the bone-contacting surface. The plurality of suture holes can be disposed adjacent to the plurality of suture hole. A graft hole and a plurality of fastener holes can extend between the upper surface and the bone-contacting surface. The delivery device can be configured to deliver at least one of an osteobiologic material, a graft material and a pharmacological substance to the graft hole.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from, but is not limited by, the detailed description and the accompanying drawings, wherein.

DESCRIPTION OF VARIOUS ASPECTS

Figure 1:
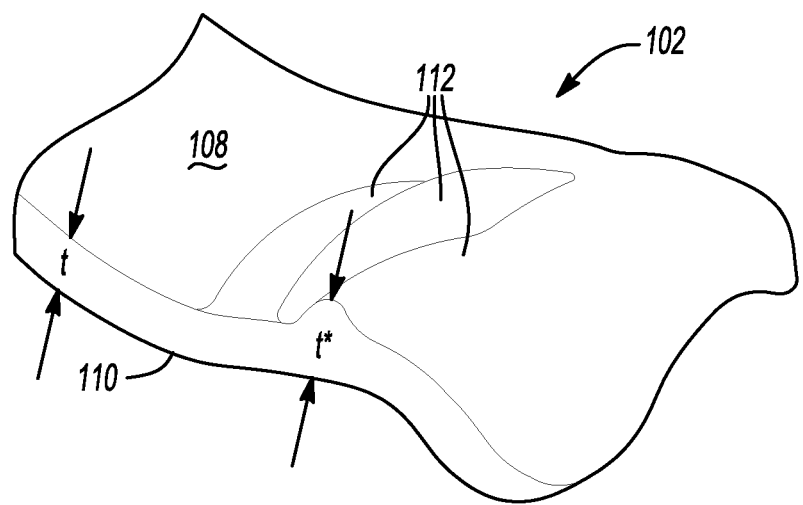
FIG. 1 is a simplified partial perspective view showing only the contour of a bone plate according to the present teachings.
Figure 2:
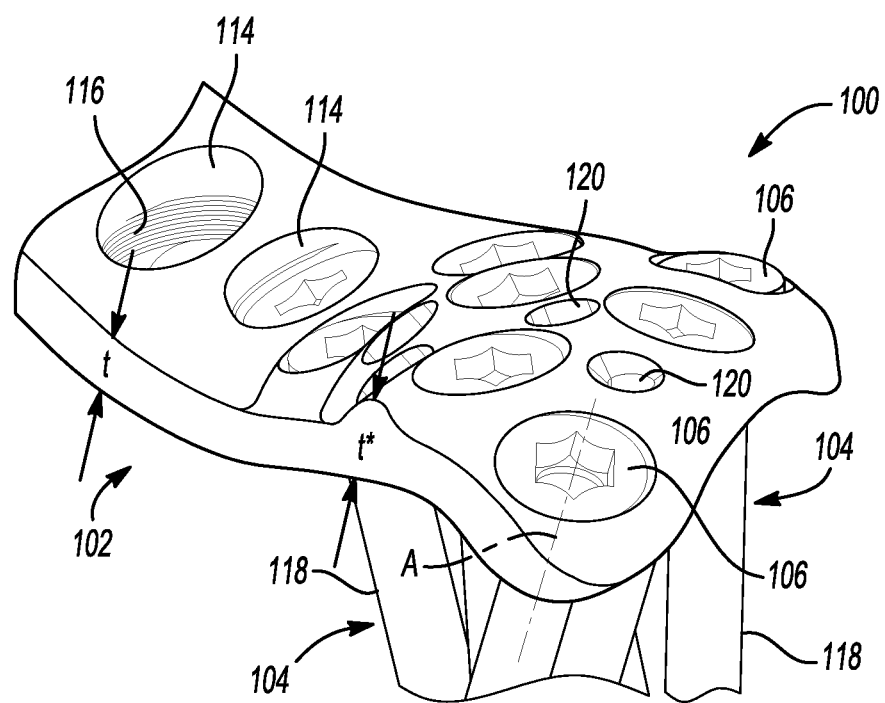
FIG. 2 is a partial perspective view of a plate assembly according to the present teachings.

The following description is merely exemplary in nature and is in no way intended to limit the invention, its applications, or uses. For example, the present teachings can be used for various plating systems, including, but not limited to, systems for the proximal tibia, the distal tibia, the proximal femur, the distal radius, the humerus, and the elbow.

Referring to FIGS. 1-13, exemplary bone plate assemblies 100 according to the present teachings are illustrated. The bone plate assembly 100 can include a bone plate 102 that has a bone-contacting lower surface 110 and an opposite upper surface 108. The bone-contacting surface 110 can be shaped to substantially or generally conform or mate with a corresponding plate-contacting surface of the bone 80. Referring to FIG. 5, the upper surface 108 can be substantially parallel to the lower surface 110 defining a nominal thickness "t", except in selected surface regions 112, in which the upper surface 108 has been modified to define an increased thickness t*, as explained below.

Figure 8:
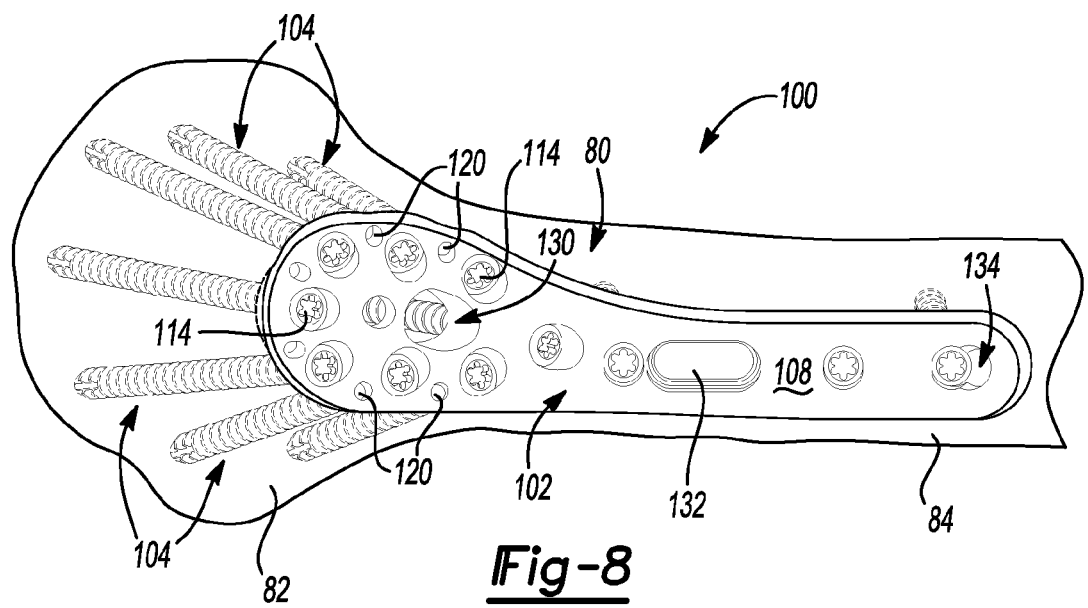
FIG. 8 is an environmental top view of a plate assembly according to the present teachings, shown operatively associated with a bone.
Figure 11:
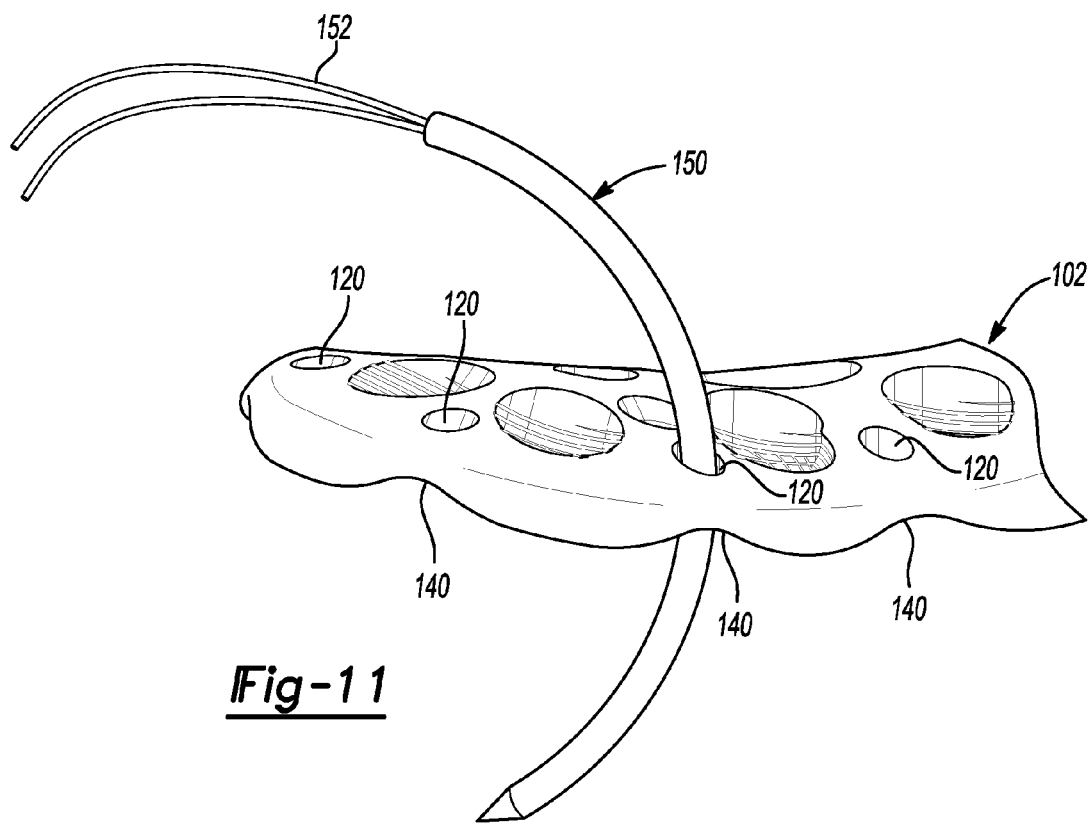
FIGS. 11 and 12 are perspective views of a bone plate shown with a suturing instrument according to the present teachings.
Figure 12:
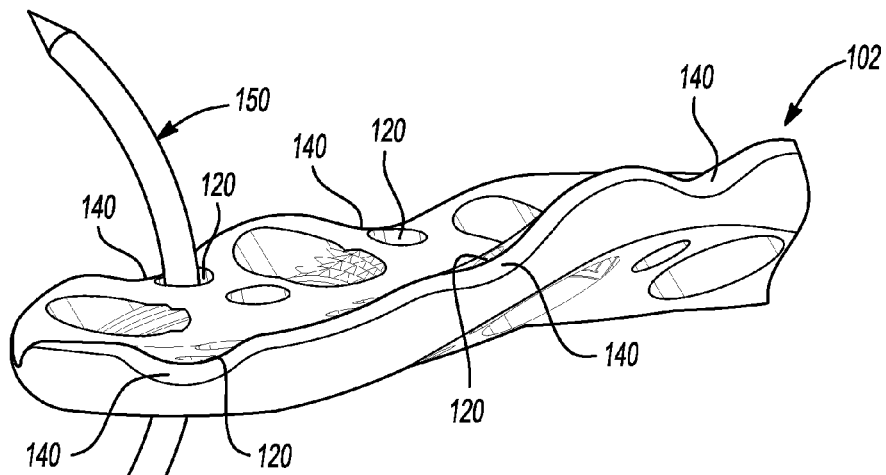
Figure 13:
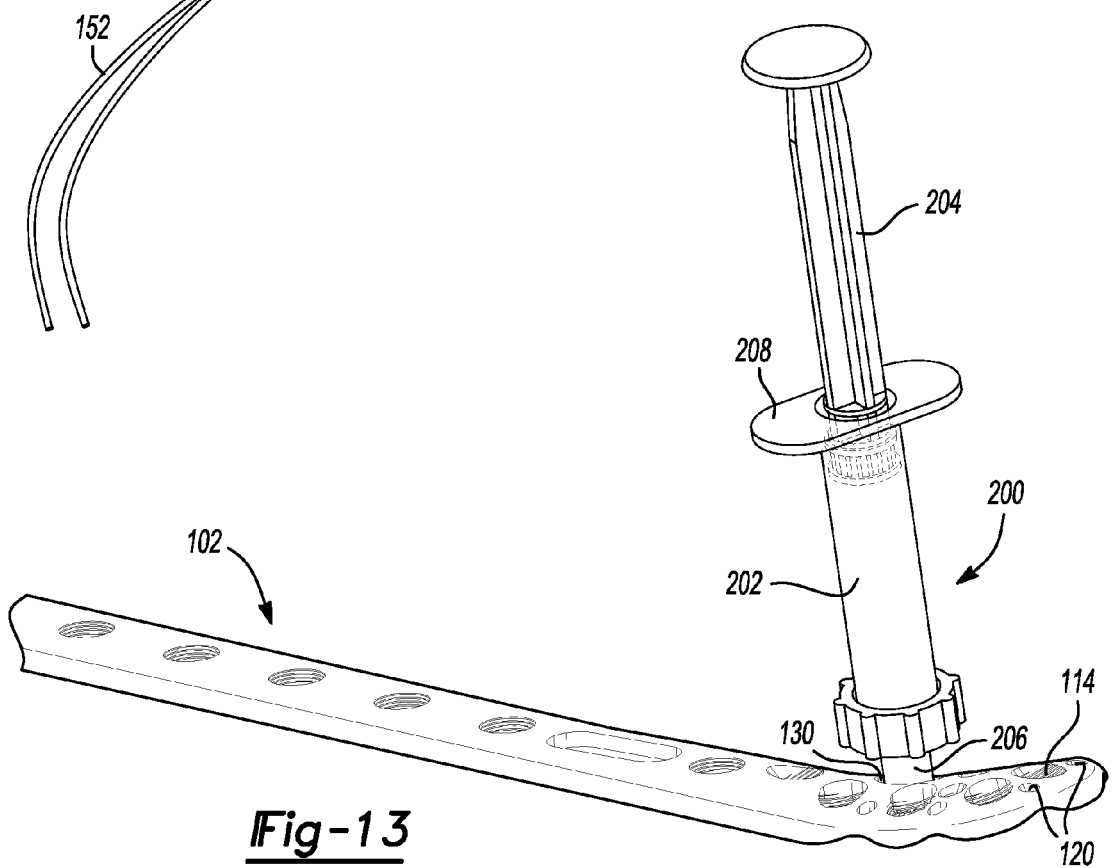
FIG. 13 is a perspective view of a bone plate shown with a graft delivery device according to the present teachings.

The bone plate 102 can include one or more fastener holes 114 for receiving corresponding bone fasteners 104, and one or more suture holes 120 for receiving sutures and/or guide wires. The suture holes 120 can be unthreaded and define smooth inner wall for reducing suture damage. The suture holes 120 can be of a size adequate for passing a suture 152 with a suture instrument 150, as shown in FIGS. 11 and 12. The suture holes 120 can be of smaller diameter than the fastener holes 114. Referring to FIG. 8, the bone plate 102 can also include at least one large non-threaded graft hole 130 for injecting osteobiologics for bone graft applications with a delivery device 200, as shown in FIG. 13. The graft hole 130 can be larger in diameter than the fastener holes 114. The delivery device 200 can be, for example, syringe-like, and can include an outer tube 202 and a plunger 204 slidably received in the tube 202. The outer tube 202 can include a proximal stop flange 208 and a distal tip portion 206. The delivery device 200 can be loaded with the osteobiologic or other graft or pharmacological substance, and the tip portion 206 can be inserted through the graft hole 130. The plunger 204 can be pushed toward the stop flange 208 expelling the substance through the tip portion 206.

The bone plate 102 can also include a fully threaded elongated slot 132, and an opening 134 formed by two communicating threaded holes for providing the surgeon with choice of two different trajectories for the bone fasteners 104, as shown in FIGS. The fastener holes 114 can be threaded and configured so that they can be used with locking or non-locking bone fasteners 104. Each bone fastener 104 can include a head 106 and a bone engaging portion 118. The head 106 can be threaded for locking applications, or unthreaded for non-locking applications. The fastener holes 114 and the heads 106 of the bone fasteners 104 can cooperate by their corresponding threads or other interconnection systems, such as integral or modular interlocking devices including expandable rings, various slotting arrangements, and others, such that the bone fasteners 104 can be locked in a pre-determined orientation, as shown in FIG. 4, or, in other aspects, allowed to angulate. As illustrated in FIG. 4, the threads 116 can be oriented at an angle relative to the upper surface 108 of the plate 102, such that the bone fastener 104 can extend along a predetermined direction A defining a trajectory for the orientation of the head 106 of the bone fastener 104.

Figure 3:
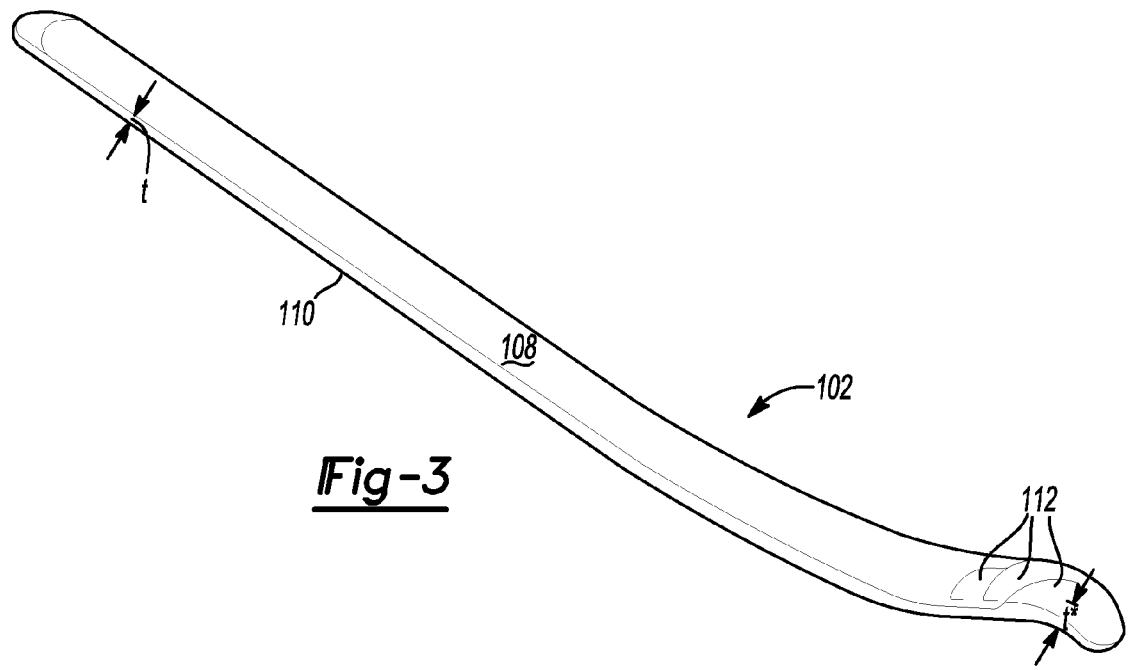
FIG. 3 is a simplified full perspective view of the bone plate shown in FIG. 1.
Figure 4:
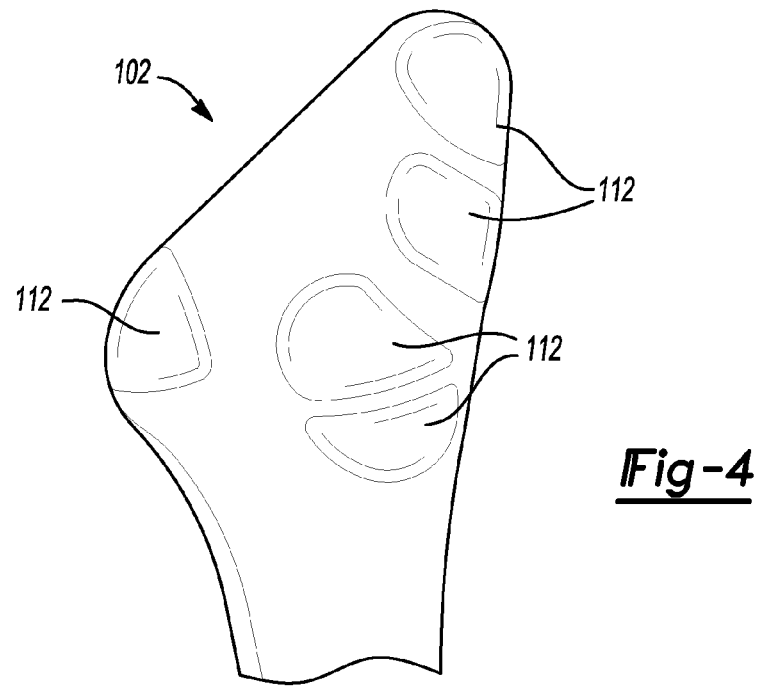
FIG. 4 is a plan view of a portion of the bone plate shown in FIG. 1.
Figure 5:
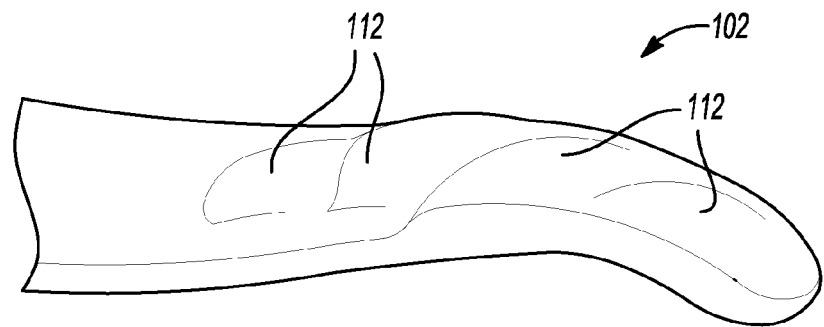
FIG. 5 is a partial side perspective view of the bone plate shown in FIG. 3.
Figure 6:
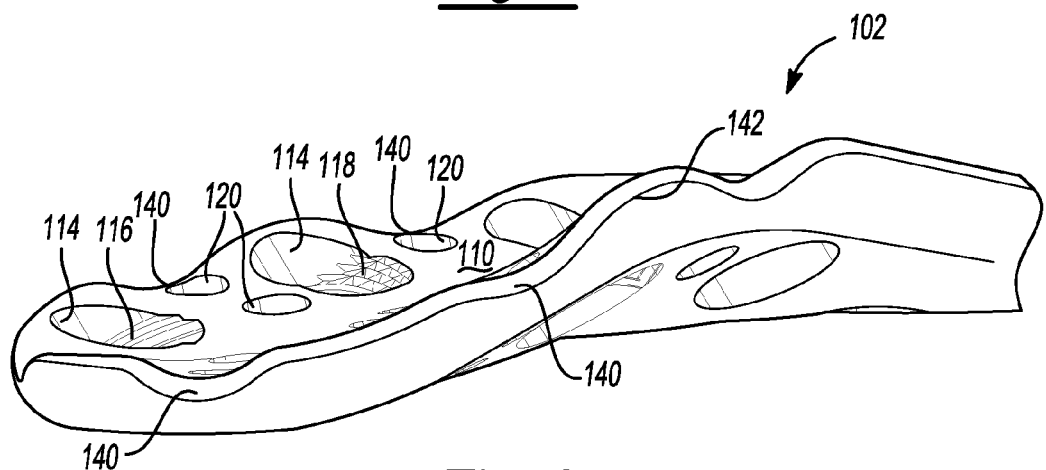
FIG. 6 is a bottom perspective view of a portion of a bone plate according to the present teachings.
Figure 7:
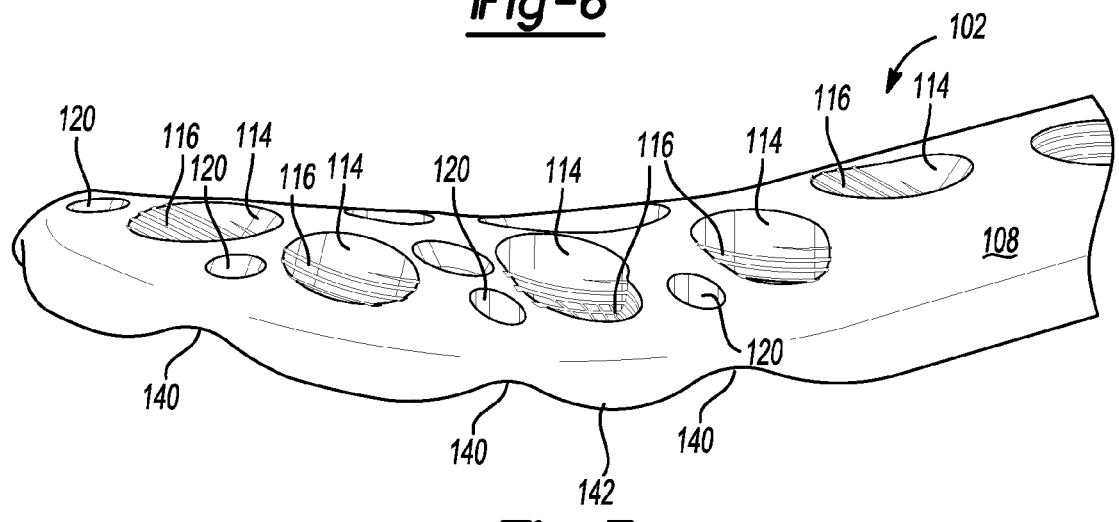
FIG. 7 is a top perspective view of the bone plate of FIG. 6.

Referring to FIGS. 3 and 4, the upper surface 108 of the bone plate 102 can be modified to create the surface regions 112 which are shaped such that when the bone fasteners 104 are inserted through the corresponding fastener holes 114, the heads 106 of the bone fasteners 104 do not protrude above the modified upper surface 108 of the bone plate 102. In other words, the heads 106 of the bone fasteners 104 are flush with, or recessed, with respect to adjacent portions of the upper surface 108. For example, material can be added to the bone plate 102 in a manner that follows the expected trajectory of the head 106 of the fastener 104 throughout a range of orientations, or generally in a manner such that the head 106 remains at or below the upper surface 108 of the bone plate 102 without diminishing the thickness of the bone plate 102 or compromising its strength. It will be appreciated that the upper surface 108 of the bone plate 102 can be modified by various methods, including computer-aided processes that determine the expected trajectories of the heads 106 and determine the modifications required for the profile of the bone plate 102 to avoid protrusion of the heads 106 above the upper surface 108 of the bone plate 102, thereby creating the surface regions 112 which have increased thickness t* relative to the nominal thickness t. It will be appreciated that the bone plate assembly 100 of the present teachings may help reduce or substantially eliminate impingement of the heads 106 of the bone fasteners 104 on the surrounding soft tissues.

Referring to FIGS. 6-12, the bottom surface 110 of the bone plate 102 can define suture-clearance formations 140 placed in relative proximity with corresponding suture holes 120 for facilitating suturing the bone plate 102 through the suture holes 120 and onto muscle tissue associated with the bone 80 in various surgical repair procedures, such as, for example, rotator cuff or other shoulder procedures. The suture-clearance formations 140 can be located and configured for providing easy access to a suturing instrument 150 carrying a suture 152, and allowing clearance for suturing manipulation, as shown in FIGS. 11 and 12. The suture-clearance formations 140 can be in the form of undulations or recesses sized to accommodate passing of the suturing instrument 150, which can be a curved or straight suturing needle, for example. Each suture-clearance formation 140 can extend from a perimeter 142 of bone-contacting surface 110 toward one of the suture holes 120. The shape and placement of the suture-clearance formations 140 in relation to the suture holes 120 can facilitate manipulation of the suturing instrument 150 by the operating surgeon. The suture-clearance formations 140 can define an undulating or wavy shape on the perimeter 142 of the bone-contacting surface 110.

Figure 9:
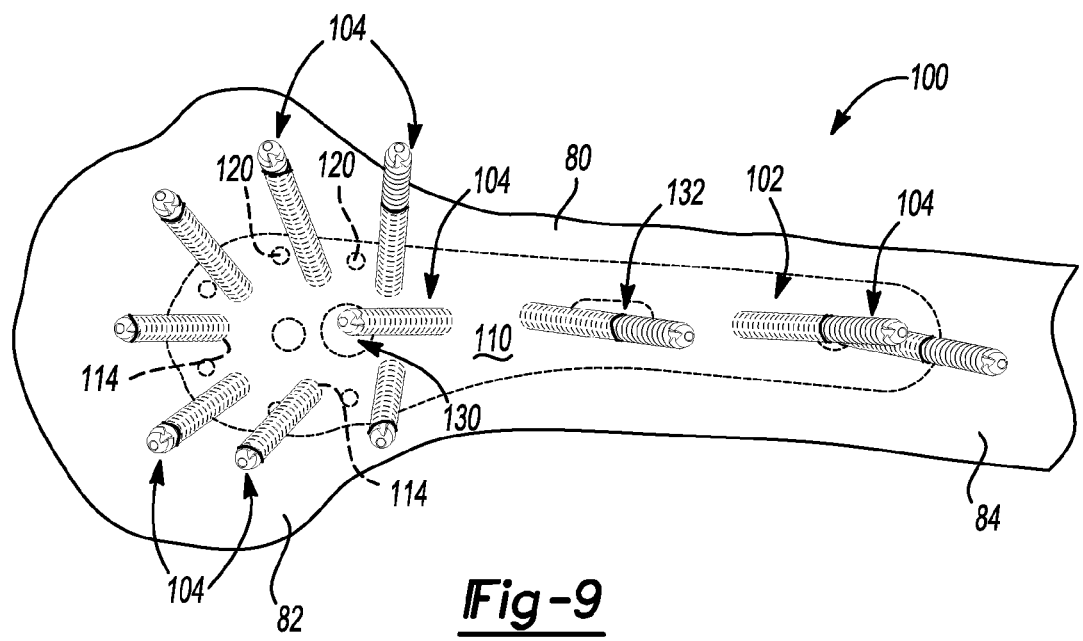
FIG. 9 is an environmental bottom view of the plate assembly of FIG. 8, shown operatively associated with a bone.
Figure 10:
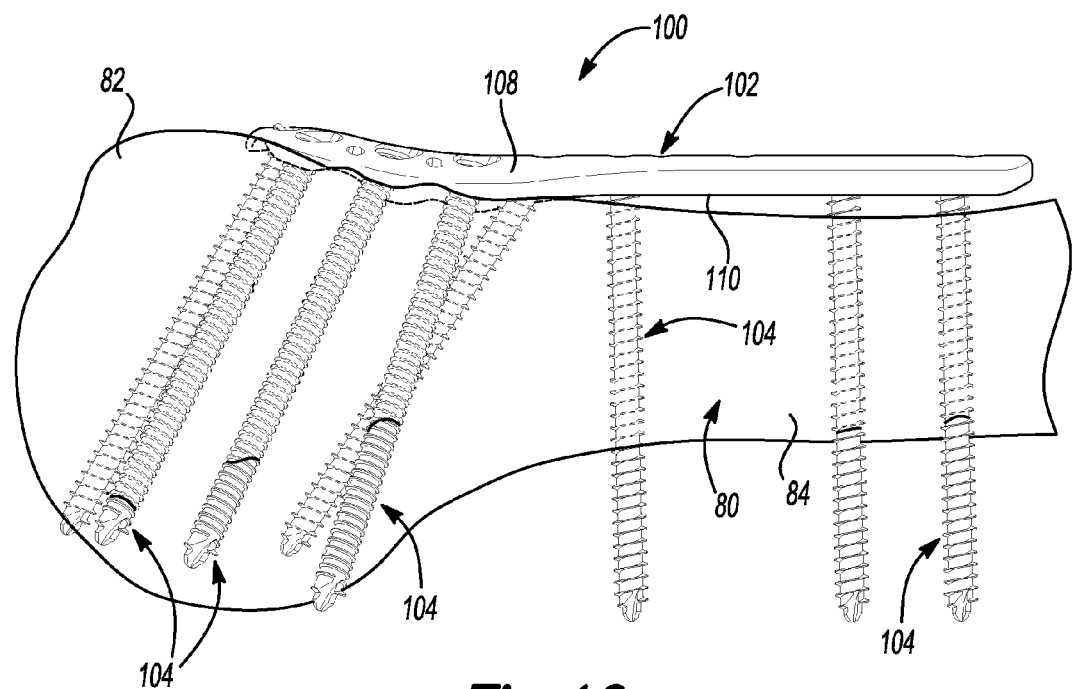
FIG. 10 is an environmental side view of the plate assembly of FIG. 8, shown operatively associated with a bone.

Referring to FIGS. 8-10, the holes 114 can provide threading configured and oriented such that the trajectories of the bone fasteners 104 can follow the shape of the underlying bone portion, such as the humeral head 82, the humeral shaft 84, or other bone portion. The orientation of the bone fasteners associated with the humeral head 82, for example, can be at an angle of 30-45 degrees relative to the orientation of the bone fasteners associated with the shaft 84, as shown in FIG. 10.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention.

What is claimed is:

1. A method for repairing a bone, the method comprising:
    attaching a bone plate to the bone, the bone plate including an upper surface, a bone-contacting surface, at least one suture hole, and at least one graft hole, each of the at least, one suture hole and the at least one graft hole extending between the upper surface and the bone-contacting surface, at least a portion of a perimeter of the bone contacting surface having a continuously undulating shape including a series of alternating convex regions and concave regions, the concave regions extending away from the bone contacting surface, wherein the undulating shape defines at least one suture clearance formation, the least one suture hole disposed adjacent to a concave region of the undulating shape;
    inserting at least a portion of a delivery device into the at least one graft hole, the delivery device including at least one of an osteobiologic material, a graft material and a pharmacological substance; and injecting the at least one of the osteobiologic material, the graft material and the pharmacological substance into the bone and through the at least one graft hole.

2. The method of claim 1, wherein the delivery device includes a syringe having an outer tube and a tip portion, and wherein the at least one of the osteobiologic material, the graft material and the pharmacological substance is disposed within the outer tube, the method further comprising:

inserting the tip portion into the at least one graft hole; and delivering the at least one of the osteobiologic material, the graft material and the pharmacological substance into the bone from the outer tube to the at least one graft hole through the tip portion.

3. The method of claim 2, further comprising loading the outer tube with the at least one of the osteobiologic material, the graft material and the pharmacological substance.

4. The method of claim 1, wherein the bone plate includes a fastener hole extending between the upper surface and the bone-contacting surface, the method further comprising inserting a fastener through the fastener hole.

5. The method of claim 4, further comprising inserting the fastener into the bone.

6. The method of claim 5, wherein the fastener includes a bone screw.

7. The method of claim 6, further comprising threadingly engaging a head portion of the fastener with a threaded portion of the fastener hole.

8. The method of claim 7, further comprising varying an angle of the fastener in the fastener hole relative to the bone plate.

9. The method of claim 4, further comprising inserting the fastener into a muscle tissue.

10. The method of claim 9, wherein the fastener includes a suture.

11. A method for implanting a bone plate, the method comprising: attaching the bone plate to a bone, the bone plate including an upper surface, a bone-contacting surface, a fastener hole, a suture hole, and a graft hole, the fastener, suture and graft holes extending between the upper surface and the bone-contacting surface, at least a portion of a perimeter of the bone contacting surface having a continuously undulating shape including a series of alternating convex regions and concave regions, the concave regions extending away from the bone contacting surface wherein the undulating shape defines a suture clearance formation, the suture hole disposed adjacent to a concave region of the undulating shape;

inserting a fastener through the fastener hole and into the bone; inserting a suture through the suture hole;

providing a syringe having a tip portion, an outer tube, and a plunger;

loading the outer tube with at least one of an osteobiologic material, a graft material and a pharmacological substance;

inserting the tip portion of the syringe into the graft hole; and injecting the at least one of the osteobiologic material, the graft material and the pharmacological substance through the tip portion and into the graft hole.

12. The method of claim 11, further comprising threadingly engaging a head portion of the fastener with a threaded portion of the fastener hole.

13. The method of claim 12, further comprising varying an angle of the fastener in the fastener hole relative to the bone plate.

14. An orthopaedic assembly comprising:

a bone plate including an upper surface, a bone-contacting surface, the upper surface and the bone-contacting surface cooperating to define a nominal thickness of the bone plate, at least a portion of a perimeter of the bone contacting surface having a continuously undulating shape including a series of alternating convex regions and concave regions, the concave regions extending away from the bone contacting surface wherein the undulating shape defines a plurality of suture-clearance formations providing a clearance between the bone-contacting surface of the bone plate and the bone, the bone plate further including;

a plurality of suture holes extending between the upper surface and the bone-contacting surface, wherein each of the plurality of the suture holes is and disposed adjacent to a concave region of the undulating shape;

a plurality of fastener holes extending between the upper surface and the bone-contacting surface; and a graft hole extending between the upper surface and the bone-contacting surface; and a delivery device configured to deliver at least one of an osteobiologic material, a graft material and a pharmacological substance to the graft hole.

15. The orthopaedic assembly of claim 14, wherein the delivery device includes a tip portion configured to be disposed within the graft hole.

16. The orthopaedic assembly of claim 14, wherein the delivery device includes a syringe.

17. The orthopaedic assembly of claim 16, wherein the syringe includes a tip portion configured to be disposed within the graft hole.

18. The orthopaedic assembly of claim 16, wherein the syringe includes an outer tube and a plunger slidably received in the outer tube.

19. The orthopaedic assembly of claim 18, wherein the at least one of the osteobiologic material, the graft material and the pharmacological substance is disposed within the outer tube.

20. The orthopaedic assembly of claim 14, wherein the upper surface includes a plurality of raised portions having a greater thickness than the nominal thickness the plurality of fastener holes positioned relative to the plurality of raised portions such that fasteners respectively received within the plurality of fastener holes are flush with or recessed from the upper surface.

* * * * *

UNITED STATES PATENT AND TRADEMARK OFFICE
CERTIFICATE OF CORRECTION

PATENT NO. : 9,750,550 B2  
APPLICATION NO. : 14/564185  
DATED : September 5, 2017  
INVENTOR(S) : Leung et al.

Page 1 of 1

It is certified that error appears in the above-identified patent and that said Letters Patent is hereby corrected as shown below:

In the Claims

In Column 4, Line 59, in Claim 1, delete "bone contacting" and insert --bone-contacting-- therefor In Column 4, Line 62, in Claim 1, delete "bone contacting" and insert --bone-contacting-- therefor In Column 4, Line 64, in Claim 1, after "the", insert --at--

In Column 5, Line 38, in Claim 11, after "comprising:", insert --¶--

In Column 5, Line 43, in Claim 11, delete "bone contacting" and insert --bone-contacting-- therefor In Column 5, Line 46, in Claim 11, delete "bone contacting" and insert --bone-contacting-- therefor In Column 5, Line 51, in Claim 11, after "bone;", insert --¶--

In Column 6, Line 12, in Claim 14, delete "surface," and insert --surface and-- therefor In Column 6, Line 15-16, in Claim 14, delete "bone contacting" and insert --bone-contacting-- therefor In Column 6, Line 19, in Claim 14, delete "bone contacting" and insert --bone-contacting-- therefor In Column 6, Line 19, in Claim 14, after "surface", insert --,--

In Column 6, Line 26, in Claim 14, before "suture", delete "the"

In Column 6, Line 53, in Claim 20, after "thickness", insert --,--

Signed and Sealed this  
Eighteenth Day of June, 2019

Andrei Iancu  
*Director of the United States Patent and Trademark Office*